US00PP10146P

United States Patent [19]

Caldwell

[11] Patent Number: Plant 10,146

[45] Date of Patent: Dec. 9, 1997

[54] SPATHIPHYLLUM PLANT 'BOND B'

[76] Inventor: E. Bond Caldwell, 18444 Townsend House Rd., Dade City, Fla. 33523

[21] Appl. No.: 690,078

[22] Filed: Jul. 31, 1996

[51] Int. Cl.[6] ..... A01H 5/00

[52] U.S. Cl. ..... Plt./88.1

[58] Field of Search ..... Plt./88.1

*Primary Examiner*—James R. Feyrer

*Attorney, Agent, or Firm*—Rothwell, Figg, Ernst & Kurz

[57] ABSTRACT

A new and distinct cultivar of Spathiphyllum is provided. It is a medium size, full plant, suitable for production in a 20–25 cm pot; branches freely; has relatively large, dark green, glossy, thick leaves. Medium to large spathes are held on strong peduncles moderately high above foliage.

2 Drawing Sheets

SUMMARY OF THE INVENTION

This invention relates to a new and distinct Spathiphyllum cultivar characterized by the following combination of repeatedly observed traits:

1. Medium size,
2. full growth habit,
3. abundant branching,
4. relatively large, dark green, thick, glossy leaves,
5. medium to large spathes, held moderately high above foliage on strong peduncles;

and primarily selected for those characteristics being so selected from the progeny of the cross stated below being grown near Altha, Fla. in a cultivated area.

ORIGIN AND ASEXUAL REPRODUCTION

Asexual reproduction of this cultivar by tissue culture was directed by me, such reproduction establishing that the plant does in fact maintain the characteristics described in successive generations.

The plant was initially selected in a planned breeding program in a cultivated area in Dade City, Fla. It has been reproduced by tissue culture in the vicinity of Altha, Fla. since 1992 with the characteristics stated. The female was Spathiphyllum 'Alice' and the male parent was *Spathiphyllum wallisii*. The cross was made in 1987 and the seedling was selected in 1989.

This new cultivar has been identified as Spathiphyllum 'Bond B'. It is possible that other identification will be adopted in the trade, but the name selected will serve for the purposes hereof.

BRIEF DESCRIPTION OF THE PHOTOGRAPHS

The accompanying photographs show as nearly true as it is reasonably possible, in a color illustration of this character, typical specimens of the plant parts of the new cultivar. The plant of 'Bond B' was approximately 15 months from planting a tissue cultured microcutting and grown in a 20 cm pot.

In the photographs:

DETAILED DESCRIPTION OF THE NEW CULTIVAR

Figure 1:
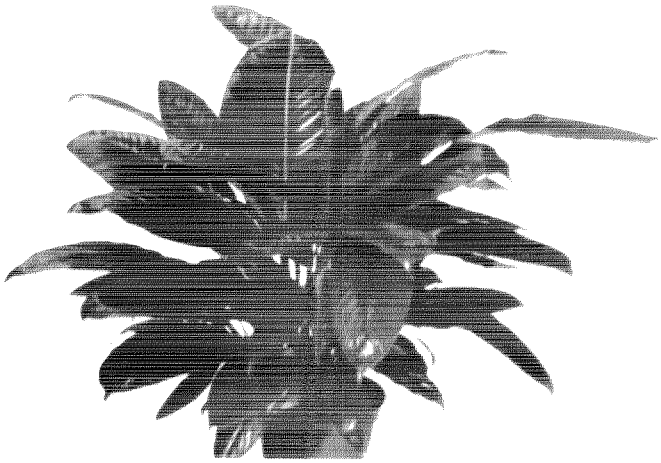
FIG. 1 depicts the whole plant.
Figure 2:
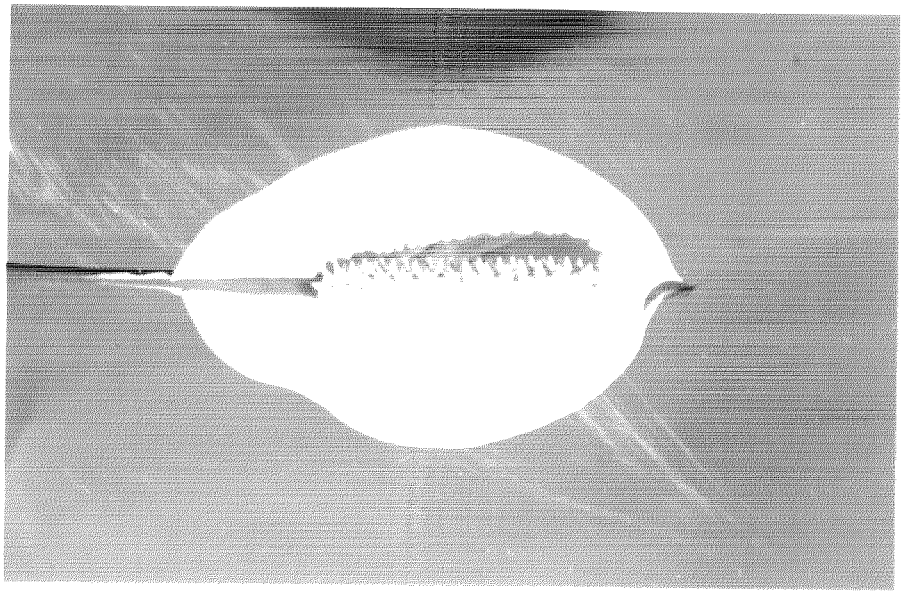
FIG. 2 illustrates the mature inflorescence.
Figure 3:
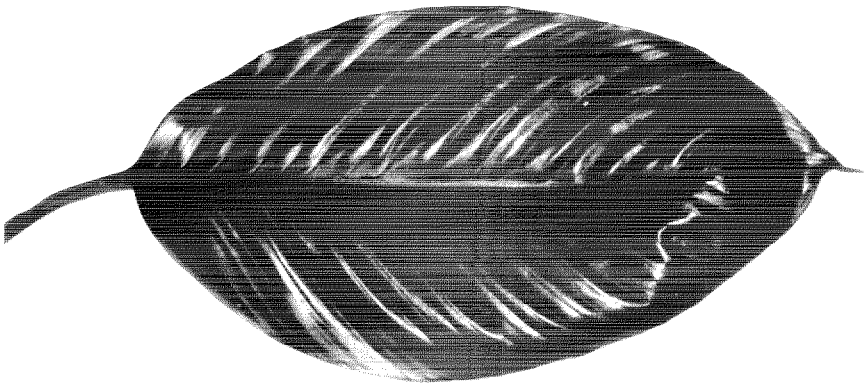
FIG. 3 illustrates the top of a mature leaf.
Figure 4:
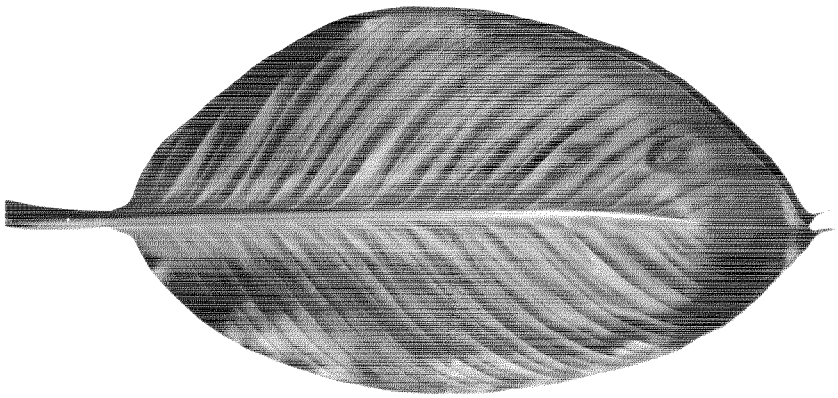
FIG. 4 illustrates the bottom of a mature leaf.

The following observations and measurements describe plants grown near Altha, Fla. under greenhouse conditions. These observations and measurements were recorded in October, 1995 from mature plants (about 15 months from planting tissue cultured microcuttings) grown in 20 cm pots. Fully developed organs were used for measurements. Two types of leaves were measured: a leaf at the base of an inflorescence (further called a flower leaf) and the preceding leaf (further called a non-flower leaf). Color values were determined or Oct. 5, 1995, under natural, indirect light of approximately 400 foot-candles. Color references are made to the RHS Color Chart, except where general color terms of ordinary significance are used.

'Bond B' has not been observed under all possible environmental conditions. The phenotype may vary with variations in environment and horticultural practices, such as temperature, light intensity, day length, fertilization, propagation method, etc., without any change in genotype.

Parentage:

*Female parent.*—Spathiphyllum 'Alice'.

*Male parent.*—*Spathiphyllum wallisi.*

Propagation: Plant tissue culture.

Plant:

*Growth habit.*—Medium size, full, well branched, with a dominant main stem.

*Height.*—*Foliage* 52–58 cm, with spathes 72–82 cm.

*Diameter.*—79–84 cm.

Petiole:

*Size.*—Flower leaf: 30.3–35.5 cm long, 4.4–5.0 mm in diameter (immediately below geniculum).

Non-flower leaf: 26.7–31.0 cm long, 5.0–5.7 mm in diameter immediately below geniculum).

*Geniculum.*—Flower leaf: 3.9–4.7 cm long 5.4–6.2 mm in diameter. Non-flower leaf: 4.0–4.7 cm long, 6.0–7.3 mm in diameter.

Leaf blade:

*Shape.*—Elliptic to ovate, asymmetric in respect to midrib, slightly convex with sunken midrib; base: between cuneate and obtuse, narrowly decurrent on peduncle; tip: acuminate with aristate tendencies, usually curved down, asymmetric and sometimes slightly cuspidate on one side. Leaf blades on side shoots are usually narrower and flatter, with more cuneate bases.

*Size*—Flower leaf: 29.5–35.5 cm long by 14.7–18.2 cm wide; length: width ratio 1.8–2.1:1.

Non-flower leaf: 30.0–39.5 cm long by 15.9–19.9 cm wide; length: width ratio 1.8–2.2:1.

*Texture.*—Leathery, smooth, glossy; young leaves polished.

*Veins.*—Well defined and sunken in the adaxial leaf surface.

*Color.*—Mature leaf: Adaxial: much darker than 147A; veins the same color. Abaxial: lighter than 147B. Veins: midrib 144A at the base, becomes lighter distally—144B at mid length, similar to 147D beyond ¾ length, except for the tip, where it is darker than the surrounding tissue. Segments of primary veins close to midrib approximately 144B. Newly unfolded leaf: Adaxial: greener than 146A; veins the same color. Abaxial: similar to 147B, 147C and 138B. Veins: most of midrib and segments of primary veins close to midrib similar to 147D.

Inflorescence: Inflorescences carried moderately high above foliage on strong, usually straight peduncles.

Peduncle:

*Size.*—62.0–70.0 cm long (including stipe), 4.3–6.2 mm in diameter immediately below spathe; peduncle slightly thins approximately 7–8 cm below spathe.

*Color.*—Front: immediately below spathe most similar to, but lighter and more gray than 143C with some resemblance to 138B and to 144B; proximally it becomes darker—most similar to 144A at the mid length of the free portion; adjacent to petiole sheath it is sometimes lighter. Back: Varies from 144A-B to 143C immediately below spathe; darker and greener—137C and 138A at mid length of the free portion.

*Stipe.*—0.7–1.1 cm long (back side), 3.7–5.6 mm in diameter.

Spathe:

*Shape.*—Elliptic, cupped; tip: between cuspidate and acuminate with aristate tendencies, asymmetric, curled; base: between obtuse and cuneate, usually asymmetric; wings 1.2–1.9 cm long, 1.3–2.5 mm wide, narrowly decurrent on peduncle.

*Size.*—13.2–16.3 cm long by 7.8–9.9 cm wide and 1.6–2.3 cm deep; length:width ratio 1.6–1.8:1.

*Color.*—Closed bud (front mid length): a little lighter than 157A, much darker than 155A.

Mature spathe: Between 155A and 157C on both sides, with green tip and some green veins. On the back side predominant color of the proximal potion of midrib is 144A with some areas of 144B and 143C and central zone slightly lighter than the borders. The narrow distal part of the midrib is darker and more uniform in color than the proximal portion. It is 144A, except for the most distal 2–2.5 cm, which is 137A, as is most of the tip. Potions of primary veins and some secondary veins in the distal part are 144B-D. On the front side distal approximately ⅓ of midrib, the tip and primary veins close to the tip are 137A-B.

Spadix:

*Size.*—5.2–9.0 cm long; 1.6–1.9 cm in diameter.

*Color.*—Pistils 158A-B, perianth 158C-D.

Botanical flower:

*Perianth.*—Well visible between pistils, segments united.

*Pistil.*—*Relatively long and narrow; extends approximately* 4 mm beyond perianth.

*Stamens.*—not visible before pollen release.

Flowering: Approximately 15 months after planting tissue culture produced microcutting one to two white spathes present above foliage.

Spathe Longevity: Spathe remains white for up to 4.5 weeks following bud appearance above foliage and then gradually changes to a green color.

Roots: Thick, cream-brownish main roots, abundant fine lateral roots.

Disease and insect resistance: No unusual susceptibility to diseases or insects noted to date.

Comparison With The Known Cultivars

The new cultivar can be compared to the known cultivars 'Viscount' and 'Supreme'. Observations for comparisons were made on plants grown under similar conditions in a greenhouse near Altha, Fla.

'Bond B' is distinguished from 'Viscount' by its more dominant main stem; leaf blades slightly larger and more variable in shape; shorter leaf tips; slightly closer proximity of spathes to foliage; greener, usually more elongated spathes, with shorter tips and often leaning at maturity.

'Bond B' is distinguished from 'Supreme' by its earlier and more abundant branching; smaller, thicker, glossier and darker leaf blades, shorter spadixes; greener, smaller, more elliptic, less cupped, less upright spathes, with more cuneate bases.

I claim:

1. A new and distinct cultivar of Spathiphyllum plant named 'Bond B', substantially as described and illustrated herein, characterized particularly as to novelty by its medium size; abundant branching; relatively large, dark green, thick, glossy leaves and medium to large spathes held on strong peduncles moderately high above foliage.

* * * * *